United States Patent [19]

Benedek et al.

[11] Patent Number: 4,993,827
[45] Date of Patent: Feb. 19, 1991

[54] METHOD FOR DETECTING CATARACTOGENESIS

[75] Inventors: George B. Benedek, Belmont; Peter C. Magnante, West Brookfield, both of Mass.

[73] Assignee: Massachusetts Institute of Technology, Cambridge, Mass.

[21] Appl. No.: 298,275

[22] Filed: Jan. 13, 1989

Related U.S. Application Data

[63] Continuation of Ser. No. 91,834, Sep. 1, 1987, abandoned.

[51] Int. Cl.$^5$ ............................................... A61B 3/10
[52] U.S. Cl. .................................... 351/221; 351/205; 351/246
[58] Field of Search ............... 351/205, 214, 221, 246; 128/633, 745; 606/4, 5, 6

[56] References Cited

U.S. PATENT DOCUMENTS

| | | | |
|---|---|---|---|
| 4,080,264 | 3/1978 | Cohen et al. | 195/103.5 A |
| 4,327,973 | 5/1982 | Raif | 351/213 |
| 4,350,163 | 9/1982 | Ford, Jr. et al. | |
| 4,702,576 | 10/1987 | Magnante | 351/214 |
| 4,711,542 | 12/1987 | Ichihashi et al. | 351/221 |
| 4,719,912 | 1/1988 | Weinberg | 128/303.1 |

Primary Examiner—Rodney B. Bovernick
Attorney, Agent, or Firm—Seed and Berry

[57] ABSTRACT

A method is disclosed to determine the degree of cataractogenesis of a lens in vivo. By collecting and determining the intensity of light scattered from a measurement location in the lens and comparing this value to the intensity of light scattered by a normal, clear lens region or a calibrating element, it is possible to determine the degree of cataractogenesis at the specific measurement location. This data may be applied to an experimentally determined and theoretically deduced universal curve in order to determine quantitatively the degree of cataractogenesis at that particular location in the lens.

4 Claims, 3 Drawing Sheets

METHOD FOR DETECTING CATARACTOGENESIS

GOVERNMENT SUPPORT

The invention described herein was supported in whole or in part by a grant from the National Institutes of Health.

This is a continuation of application Ser. No. 091,834, filed Sept. 1, 1987, now abandoned.

BACKGROUND OF THE INVENTION

A reliable, quantitative and non-invasive method for the characterization of the molecular changes associated with early cataractogenesis in-vivo has long been an important goal of human clinical cataract research. Such a method would allow researchers and physicians to: (a) assess the effectiveness of putative anticataract reagents; (b) evaluate the cataractogenic role of pharmacologic agents or radiation used in the treatment of systematic disease; (c) characterize early cataract in epidemiologic studies of human or animal populations subject to differential cataractogenic stress; and, d) provide a quantitative basis for the medical decision to intervene surgically or pharmaceutically in the treatment of cataract.

In 1975, T. Tanaka and G. Benedek, ("Observation of Protein Diffusivity in Intact Human and Bovine Lenses with Application to Cataract," Invest. Ophthal. 14, 449-456 (1975).) showed that the Brownian motion of proteins in excised human and bovine lenses could be measured optically using the method of quasielastic light scattering spectroscopy. Following this work, T. Tanaka and C. Ishimoto, ("In Vivo Observation of Protein Diffusivity in Rabbit Lenses," Invest. Opthal. and Vis. Sci. 16, 135-140 (1977).) demonstrated in 1977 that it was possible to conduct quasielastic light scattering measurements safely in the lens of the eye of a living rabbit.

In 1984, Nishio et al., ("In Vivo Observation of Lens Protein Diffusivity in Normal and X-Irradiated Rabbit Lenses," Exp. Eye Res. 39, 61-68 (1984).) demonstrated that quasielastic light scattering could be used in vivo in the rabbit to detect changes in mean protein diffusivity as a function of position and age in the lens. Further observations showed that the cataractogenic insult of X-irradiation upon the rabbit lens produced dramatic changes in the form of the autocorrelation function of the scattered light at a very early stage in the cataractogenic process. This change in the autocorrelation function, the mathematical heart of quasielastic light scattering analysis, demonstrated that the X-irradiation was responsible for drastic changes in the diffusivity of the protein scattering elements undergoing Brownian movement within the ocular tissue. Both Nishio and the 1977 Tanaka team observed that these altered correlation functions had a form different from that expected for the Brownian motions of a single type scatterer. However, neither undertook a quantitative analysis of the information contained in the non-exponential character of the autocorrelation function observed.

In 1986, T. Libondi et al., ("In Vivo Measurement of the Aging Rabbit Lens Using Quasielastic Light Gathering," Curr. Eye Res., Vol. 5, 6, 411-419 (1986).) showed that the form of the autocorrelation function of the scattered light from a living rabbit eye indicated the presence of at least two distinct diffusing species within the rabbit lens. One species' had a diffusivity corresponding to the α-crystalline protein. The other was a much more slowly diffusing species of the type discovered in-vitro by M. Delaye et al., ("Identification of the Scattering Elements Responsible for Lens Opacification in Cold Cataracts," Biophys. J. 37, 647-656 (1982).) in 1982.

A recently discovered method of cataract detection comprises irradiating a measurement location of a lens with a laser, collecting light scattered from the lens at the measurement location, analyzing the collected light using an autocorrelator or spectrum analyzer to determine the relative amount of light scattered from different protein species in the lens, and analyzing this data to determine the degree of cataract formation at the measurement location in the lens. A more detailed description of the method is given in copending Application Ser. No. 07/091,658; filed Sept. 1, 1987 now abandoned.

SUMMARY OF THE INVENTION

The present invention provides a method for non-invasive in-vivo inspection of ocular tissue. More specifically, a laser is used to provide a low power, coherent and uniform beam of light which is guided to a measurement location in the eye of a subject for scattering by ocular protein molecules. The scattered light is viewed and a portion of it is collected. The intensity of the light scattered by the measurement location is determined and this value is compared to a value representative of the intensity of light scattered by a normal, clear, lens region. By determining the intensity of light scattered from the measurement location and comparing it to a standard value, it is possible to accurately and quantitatively estimate the degree of cataractogenesis occurring in that location of ocular tissue.

Thus, the present invention pertains to a method for in-vivo inspection of ocular tissue comprising:
(a) providing a source of substantially monochromatic, coherent, collimated light;
(b) focusing light from the source on a first measurement location of a subject's ocular tissue;
(c) determining the intensity of light scattered by the ocular tissue at the measurement location ($I_{tot}$);
(d) comparing the value of $I_{tot}$ to a value representative of the intensity of light scattered by a normal clear lens ($I_f^o$); and,
(e) using the numerical value of the ratio $I_{tot}/I_f^o$ to determine the degree of cataract development at the specific site.

The method for in-vivo inspection of ocular tissue described herein has a number of advantages over currently known techniques for determining the degree of cataractogenesis. Unlike the present method, visual observation of the eye lens using a slit lamp microscope is not a quantitative method, nor is it sensitive enough to detect the earliest changes in scattered light produced by the first stages of cataract formation. Current photographic methods are useful for characterizing later stages of cataractogenesis. However, the instrumentation is expensive and insensitive to early cataractogenic changes due to the logarithmic response of photographic film.

The above and other features of the invention including various novel details of combination of parts will now be more particularly described and pointed out in the claims. It will be understood that the particular cataractogenesis detection method embodying the invention is shown by way of illustration only and not as

DETAILED DESCRIPTION OF THE INVENTION

Figure 1:
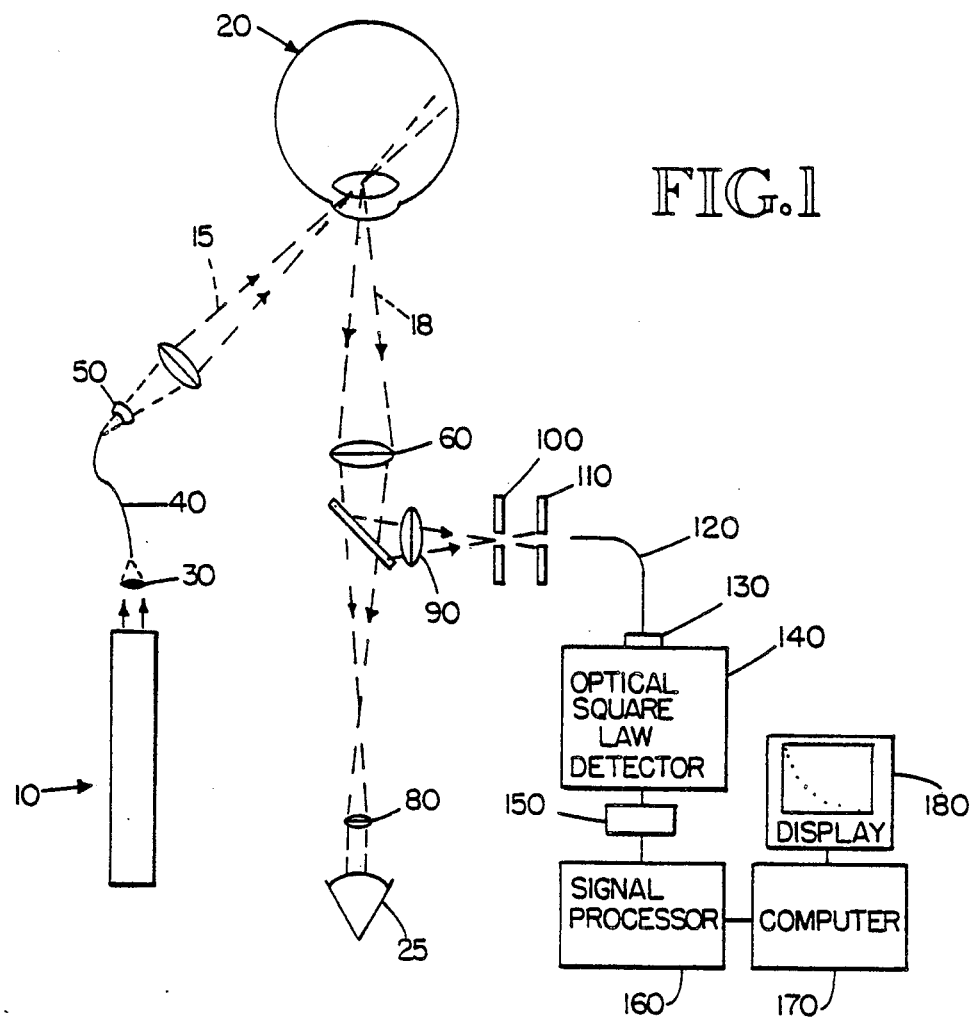
FIG. 1 is a schematic representation of an optical scattering analyzer for the study of the temporal fluctuations of laser light scattered from the lens in vivo.

The proteins present in ocular tissue undergo random diffusive movement due to continuous collisions with nearby molecules. When a coherent, steady beam of light is scattered by the moving proteins, the intensity of the scattered light fluctuates in time. The movements of the proteins determine the rate of intensity fluctuation. As it has been determined that small proteins generally diffuse faster than larger proteins or protein aggregates, it is possible to examine the detector current fluctuations to determine the relative intensity of light scattered from the small protein species and the large protein species within the lens tissue, and to determine as well the relative amounts of these two species and their individual diffusivities.

The aggregation of small proteins within the lens is the very first stage in the process of cataractogenesis. By using information obtained from the light scattered by the various fast and slow moving protein species, it is now possible to interpret, in a clear and unambiguous manner, the meaning of the components contained in the autocorrelation function or the power spectrum. This information may be used to generate an algorithm which provides a universal curve for cataract development. By locating the position on this curve corresponding to each selected position in the lens, it is possible to characterize in a very simple manner the precise degree of cataractogenesis occurring at that selected point in the lens. In effect, this invention permits the decoding of the information contained in the random intensity fluctuations in the light scattered from the lens. When placed on the disclosed universal curve, the decoded information has been shown clinically to provide an accurate quantitative measure of cataract development on a molecular level long before it could be detected visually by either the subject or the physician.

Brownian motion is defined as the motion of macromolecules caused by thermal agitation and the random striking by neighboring molecules in a solution. In the lens of the human eye, protein molecules undergoing Brownian motion may be recorded and analyzed by quasielastic light scattering.

In quasielastic light scattering (QLS), the temporal fluctuations in intensity of light scattered by a selected small volume in the lens which is illuminated by an incident laser beam are studied. The scattered light intensity fluctuates in time because of the Brownian motion of the scattering elements. In the case in which the laser beam illuminates the lens of the eye, the scattering elements are the molecular constituents of the fiber cells within the lens. These constituents are principally globular proteins called crystallins.

The light intensity fluctuations are detected by collecting the light scattered from a well-defined, illuminated volume in the eye lens and focussing this light onto the surface of an optical square law detector such as a photomultiplier tube or solid-state photodiode. The output of the detector is a photo-electric current whose temporal fluctuations are in synchrony with the fluctuations in the scattered light intensity. The temporal fluctuation in the photocurrent can be analyzed mathematically by obtaining the autocorrelation function or the power spectrum of the photocurrent. From the mathematical form of the autocorrelation function or the power spectrum of the photocurrent, it is possible to determine the diffusivity of the scattering elements undergoing Brownian movement.

The autocorrelation function may be determined by using an autocorrelator to analyze the fluctuations in the intensity of the laser light scattered by the ocular tissue Correspondingly, the power spectrum may be determined using a spectrum analyzer. The random motions of the crystalline proteins within the lens give rise to concentration fluctuations, which in turn give rise to fluctuations in the intensity of the scattered light. This scattered light may be recorded in the form of a time correlation function, the autocorrelation function $G(\tau)$, which relates the scattered light intensity at a time t, I(t), to that at a certain time $\tau$ later, I (t+$\tau$), as follows:
$G(\tau) = <I(t)I(t+\tau)>$
where $<>$ denotes averaging over all starting times t.

The photocurrent correlation function will have a form which in first order can be expressed as consisting of two exponential functions:

$$G(\tau) = (I_f + I_s)^2 + \alpha(I_f e^{-\Gamma_f \tau} + I_s e^{-\Gamma_s \tau})^2. \qquad (1)$$

In this equation, $I_f$ is the intensity of light scattered from the fast diffusing protein species within the ocular tissue and $I_s$ is the intensity of light scattered from the slow diffusing protein species in the ocular tissue. $\Gamma_f = D_f K^2$ is the decay rate of the fast diffusing species and $\Gamma_s = D_s K^2$ is the decay rate of the slow diffusing species. $D_f$ and $D_s$ are the diffusivities of the fast and slow species respectively. $K = (4\pi n/\lambda)\sin(\theta/2)$ is the scattering vector where n=index of refraction of the lens; $\lambda$=wavelength of the laser in vacuo; and $\theta$=scattering angle. Additionally $\alpha = (1/2N)$ where N=number of coherence areas in the exit aperture of the collection optics.

The first step in the analysis is to take the experimental measurements of $G(\tau)$ and to fit it to the mathematical form represented in Eqn. 1. This mathematical fitting procedure is carried out in the computer using one of a number of well-established fitting routines. (It should be noted that in general more than two exponentials may in fact be contained in $G(\tau)$. However, because of the limited signal to noise ratio which results from a clinically desirable short measurement time, approximately (1–3 sec), the correlation function could be fit quite satisfactorily to Eqn. 1.) As a result of the fitting procedure, one deduces the fundamental parameters $I_f$ and $I_s$ and their sum $I_f + I_s = I_{tot}$.

It is possible to show that $I_f$ and $I_s$ can be related to one another using the following model for the origin of the slowly moving component. The actual distribution of protein species in the lens may be approximated as a simple bimodal distribution corresponding to a two state model for the distribution of protein mass. Let $N_f$ denote the number density (number per unit volume) of the small, fast diffusers, and let $N_s$ denote the number density of the large aggregates. Furthermore, let $M_f$ denote the molecular weight of the lighter species and $M_s$ the molecular weight of the aggregates. Since the aggregates are composed of the rapidly diffusing species, $(M_s/M_f)$ is the number of small proteins in each of the large aggregates. In a clear lens when no aggregation has occurred $N_s = O$, and all the protein is regarded as existing in an unaggregated state. Under these conditions, the corresponding number density of proteins is denoted as $N_f^\rho$. At each point in the lens, the two state model of the formation of aggregates implies the following condition:

$$N_f^\rho M_f = N_f M_f + N_s M_s. \qquad (2)$$

This equation represents simply the conservation of mass. The left hand side is the total mass density of the proteins associated with both peaks of the bimodal mass distribution. $N_f M_f$ is the mass density associated with the light mass peak. $N_s M_s$ is the mass density associated with the heavy molecular weight peak in the mass distribution. Since the protein concentration is known to vary spatially within the lens, it may be expected that $N_f^\rho$ will be a function of spatial position inside the lens. In the normal young lens it is expected that $N_s = O$ and $N_f = N_f^\rho$. With aging and early cataractogenesis, $N_f$ becomes smaller than $N_f^\rho$ and $N_s$ increases. If $N_f^\rho$ is regarded as a constant independent of age, then Eqn. (2) establishes at each time a relationship between $N_s$ and $N_f$ based on the assumption that no new protein has been produced. Of course, $N_f^\rho$ can increase with age. This is to be expected particularly in the cortex where protein expression continues with aging. On the other hand $N_f^\rho$ can be expected to be relatively independent of age in the nucleus where no gene expression is occurring.

The parameters $I_f$ and $I_s$ may be expressed in terms of $N_f$, $N_s$, $M_f$ and $M_s$. Each of the scattering elements may be regarded as being spatially distributed at random positions within the illuminated region of the lens. Under these conditions, since the size of the proteins of mass $M_f$ is approximately 100 Å (i.e. small compared to the wavelength of the light), $I_f$ is proportional to the square of the mass $(M_f)$ of the scatterers and to the concentration $N_f$ of scatterers. Thus $$I_f = k_f N_f M_f^2. \qquad (3a)$$

$k_f$ is a constant of proportionality independent of scattering angle, but dependent upon such quantities as the incident light intensity and polarization, the index of refraction of the protein compared to the mean index of the lens, and the geometric arrangement of the light collection optics in the QLS spectrometer.

In the case of the larger scattering element it is necessary to include the fact that the size of these objects can be comparable to the light wavelength. As a result, the intensity of light scattered from these will be a strong function of the scattering angle. Thus, $I_s$ may be written as:

$$I_s(\overline{R}_s, \theta) = k_s(\overline{R}_s, \theta) N_s M_s^2. \qquad (3b)$$

In this equation, $k_s(\overline{R}_s, \theta)$, the coefficient of proportionality, is expressly designated as dependent upon scattering angle $\theta$, and the mean radius $\overline{R}_s$ of the heavy scattering element. Extensive calculations have been made regarding the form of $k_s(\overline{R}_s, \theta)$ for various shapes of dielectrics. It is important to keep in mind that the angular anisotropy in the intensity of light scattered from an aggregate whose size is comparable to the light wavelength or larger can be quite large. Studies of this anisotropy factor show that the ratio of the light intensity scattered near the forward direction to that scattered towards the backward direction can range from unity for small particles to approximately 100 for aggregates having sizes of several thousand Angstroms. The scattering angle used experimentally was approximately 135°. Thus $k_s(\overline{R}_s, \theta)$ could be as much as 100 times smaller than $k_f$ if the scatterers are as large as several thousand Angstroms in size. Of course, it is possible to select scattering angles, in principle, anywhere within the back-scattering quadrant, however, the choice of angle can significantly effect $k_s$.

While the aggregates will vary in size from approximately 200 Å to approximately 1000 Å, it is only necessary to consider the largest of these since they will have the greatest effect on scattering. This allows a large amount of scattering to occur even when there are very few 1000 Å aggregates present. Since this scattering may be detected, it is possible to identify the existence of large aggregates even when there are very few present.

Apart from these considerations, it is expected that $k_s$ will also depend on light intensity and polarization, index of refraction and light collection geometry in the same way as $k_f$.

It is now possible to establish a relationship between $I_f$ and $I_s(\overline{R}_s, \theta)$, the experimentally measured parameters. The quantity $(N_f^\rho - N_f)$ represents the number density of fast component converted to aggregates. Both $I_f$ and $I_s$ can be expressed in terms of this quantity. From equation (3a) it is found that:

$$I_f = k_f[N_f^\rho - (N_f^\rho - N_f)]M_f^2,$$

thus $$I_f = I_f^o - k_f M_f^2 (N_f^\rho - N_f). \qquad (4)$$

Here $I_f^o = k_f N_f^\rho M_f^2$ is the intensity of light scattered from the fast diffusing species in the absence of any aggregation. From Eqn. (3b) it is seen that $I_s$ is proportional $N_s$. Also, this quantity is proportional to $(N_f^\rho - N_f)$ as follows from the conservation condition Eqn. (2):

$$N_s = (N_f^\rho - N_f)(M_f/M_s).$$

Using this in Eqn.(3b) gives:

$$I_s(\overline{R}_s, \theta) = k_s(\overline{R}_s, \theta) M_s M_f (N_f^\rho - N_f). \qquad (5)$$

Equations (4) and (5) express quantitatively the reduction in $I_f$ and the increase in $I_s$ which is produced by the reduction $(N_f^\rho - N_f)$ in fast diffusing species and their conversion to heavy aggregates. This conversion gives a definite relationship between $I_f$ and $I_s$ which can be obtained by expressing $(N_f^\rho - N_f)$ in terms if $I_s$ using Eqn. (5) and substituting the results in Eqn. (4) i.e.

$$I_f = I_f^o - \left[\frac{k_f}{k_s(R_s, \theta)}\right]\left[\frac{M_f}{M_s}\right] I_s \qquad (6)$$

According to this result if $I_f$ and $I_s$ are measured in the nuclear region where $N_f^0$ remains roughly constant with age, as the aggregation proceeds a plot of the values of $I_f$ and $I_s$ measured at different times will produce a straight line with a negative slope whose magnitude is S where $$((k_f M_f)/k_s(\overline{R}_s, \theta)M_s = S. \quad (7)$$

The value of the intercept in this plot at $I_s = 0$ is $I_f^0$. In general, $I_f^0$ can be expected to change with position in the lens. In the cortex where protein is being produced $I_f^0$ can be expected to change with age as well as position. The size of the fast particles can be estimated approximately 100 Å while that of the large scatterers is taken to be approximately 1000 Å. The ratio $(M_f/M_s)$ is approximately $(1/10)^3$ or $10^{-3}$. It is also possible to estimate from the angular disymmetry of the large aggregate that $[k_f/k_s(\tau)]$ is approximately $10^2$. Thus the quantity S may be roughly estimated as 0.1.

Since $I_{tot} = I_s + I_f$ is the total intensity of light scattered into the collection optics from the mobile scattering elements, it is possible to examine how $I_{tot}$ depends upon $I_s$ and $I_f$ separately:

$$(I_{tot}) = I_f + I_s. \quad (8)$$

Using Eqn (6) in the above yields:

$$(I_{tot}) = I_f^0 + \left(1 - \left[\frac{k_f}{k_s(R_s,\theta)}\right]\left[\frac{M_f}{M_s}\right]\right) I_s. \quad (9)$$

Thus a plot of $I_{tot}$ versus $I_s$ has an intercept at $I_s = 0$ of $I_f^0$, and a slope of (1-S). If the estimate of S as approximately equal to 0.1 is correct, the slope of the $I_{tot}$ versus $I_s$ graph will be somewhat less than unity. If measurements of $I_{tot}$ and $I_s$ are made at a fixed position in the lens for an ensemble of subjects at various ages and varying early stages of cataract development, the corresponding pairs of points in a graph of $I_{tot}$ versus $I_s$ are expected to fall on the straight line given by Eqn. (9). This will be true if $I_f^0$ is approximately the same for each subject, and if S remains at approximately 0.1 or less for each subject. On such a "universal curve" the positioning of a point along the vertical or $I_{tot}$ axis indicates the degree of formation of heavy aggregate species. If the measurements $I_s$ and $I_f$ indicate that $I_{tot}$ is approximately 20 $I_f^0$, such a state of aggregation is likely to produce a degree of turbidity quite apparent on visual observation. The great advantage of the present form of investigation is that it provides a linear and therefore, very sensitive measure of the earliest stages of the aggregation process well before such aggregation could be detected using either photographic or visual detection, through the slit lamp microscope. The precise value of $I_{tot}$ or $I_s$ as a function of time during the progression of the disease provides a very useful quantitative characterization of the development of the aggregates.

It is also possible to relate the increase in $I_{tot}$ to the decrease in $I_f$ as follows: Since $I_{tot} = I_f + I_s$, $I_s$ may be expressed in terms of $I_f$ using Eqn. (4) and Eqn. (5). This results in the following relationship between the measured quantities $I_f$ and $I_{tot}$:

$$I_f = [1/(1-S)]I_f^0 - [S/(1-S)]I_{tot}. \quad (10)$$

Thus a plot of the experimental values with $I_f$ as ordinate and $I_{tot}$ as abscissa should yield a straight line whose intercept at $I_{tot} = I_f^0$ is $I_f = I_f^0$ and whose slope is negative with a magnitude $S/(1-S)$. Also $I_f = 0$ when $I_{tot} = (1/S) I_f^0$. Eqn. (10) represents quantitatively the decrease in $I_f$ which results from the conversion of the lighter proteins into the heavy aggregates. The total disappearance of all the lighter proteins occurs when the total light intensity reaches a value equal to $I_f^0/S$ where S is the important parameter defined in Eqn. (7).

Experimental studies have demonstrated that the theory above does in fact describe the experimentally observed relationship between $I_{tot}$ and $I_s$ or $I_{tot}$ and $I_f$ within experimental accuracy. The experiments have provided a fundamentally important practical result shown in FIGS. 4 and 5. These figures show that a plot of $I_{tot}$ versus $I_s$ is in fact a straight line, regardless of the identity or age of the subject or the location studied along the optic axis of the lens. Thus, it is possible to label a plot of $I_{tot}$ versus $I_s$ as a universal curve. This universal curve permits a very useful method for the quantitative characterization of the degree of cataract. In an actual measurement of the photocurrent fluctuation, one determines $I_f$, $I_s$ and $I_f + I_s = I_{tot}$. One then locates the position of this point on the universal curve. The advance of cataract corresponds to movement of this point in a direction radially outward along the universal curve. A reversal of the cataractogenic process corresponds to a movement of the system point $(I_{tot}, I_s)$ towards the origin. By establishing the value of the intercept $I_{tot}(I_s=0) = I_f^0$, it is possible to construct a universal curve whose ordinate axis is $(I_{tot}/I_f^0)$ and whose abscissa is $I_s$. A lens region for which no aggregation has occurred corresponds to $(I_{tot}/I_f^0) = 1$. A lens region where so much conversion to the aggregated states has occurred so that opacification is visible clinically corresponds to $(I_{tot}/I_f^0)$ equaling approximately 30. The value of the ratio $(I_{tot}/I_f^0)$ is thus a direct measure of the degree of cataractogenesis.

In view of the fact that the universal curve is a straight line with an effective slope of unity, it becomes clear that only a single coordinate is needed to unambiguously locate a point on the curve. Thus, an experimental determination of the numerical value of the ordinate, namely the quantity $I_{tot}/I_f^0$, can provide by itself a detailed, reproducible indication of the precise degree of cataract development. As can be seen from the data in FIG. 4, the values of $I_{tot}/I_f^0$ range from unity in the case of a perfectly normal lens without cataract, to approximately 30 for a region in the lens exhibiting a large degree of cataract formation.

This invention involves the elimination of the autocorrelator or spectrum analyzer. More specifically, by measuring the intensity of light scattered from the clearest part of a subject's lens (assumed to be $I_f^0$) and by comparing this value with the intensity of light scattered from a selected measurement location of the lens ($I_{tot}$), it is possible directly to determine the degree of cataractogenesis at the measurement location. The greater the ratio of $I_{tot}/I_f^0$, the greater the number of aggregated, slowly diffusing proteins at the specific location. This method is particularly advantageous because it provides very accurate measurements with a minimum of complicated equipment. The autocorrelator has been eliminated, as have a major share of the calculations needed in conjunction with previous methods.

Alternatively, a calibrating element can be provided to preset the value of $I_f^0$ corresponding to a previously determined average value of the light scattered from normal clear regions of the lens. This value of $I_f^o$ can be obtained as the result of statistical analysis of data obtained from light scattered from normal, clear lenses. By providing such a calibrating element for $I_f^o$, two objectives are achieved. First, the necessity of accurately determining $I_f^o$ for the individual patient is obviated; and second, the resulting values of $I_{tot}/I_f^o$ are standardized. This standardization enables more reliable longitudinal studies of cataract development, as well as intercomparison between different subjects and different measurement locations in the lens. In the preferred embodiment, the calibrating element comprises a suspension of polystyrene latex spheres in water, the sphere size and concentration adjusted to allow the calibrating element to have the same turbidity as a normal, clear lens.

Turning now to the Figures, FIG. 1 is a schematic representation of an optical scattering analyzer for the study of the temporal fluctuations of laser light scattered from the lens in vivo. In FIG. 1, a source of substantially monochromatic, coherent, collimated light 10, such as a laser, delivers a light beam 15, to the subjects eye 20, through a delivery means, which may consist of, for example, a focusing lens 30 which couples the light into a fiber optic delivery cable 40, and a set of delivery optics 50. The delivery optics serve to focus the light 15 onto the subject's eye at the specific location at which the measurement is to be taken. The light must be focussed for two reasons. First, the size of the illuminated area is inversely proportional to the coherence area of the scattered light. By focusing onto a small area, a greater coherence area is obtained which allows easier measurement. Second, the incident contact area on the lens in inversely proportional to the scattering area on the retina. Thus by focusing down on the eye lens, the light going to the retina is diffused, thereby preventing retinal damage. Scattered light 18 from the eye lens, passes through a collector such as an objective lens 60 onto a beam splitter 70. The beam splitter 70 serves to allow the observer to focus and position the incident light while measuring the scattered light. Part of the beam passes through the beam splitter 70 to an ocular lens 80, which focuses the image for the observers eye 25. By observing the scattering in this manner, a physician can control the laser beam and position it at a specific location on the subjects eye 20. The portion of the scattered light which is reflected by the beam splitter 70 passes into a collection means which can consist of a relay lens 90 to focus the light reflected from the beam splitter 70, an aperture stop 100 to limit the length of the beam observed, a coherence angle aperture 110 to limit the number of coherence areas collected, a fiber optic collection cable 120, and an optical filter 130 to filter out any extraneous light from that to be measured. Light passing through the optical filter 130, is converted into a photoelectric signal by an optical square law detector 140, such as a photomultiplier tube or solid-state photodiode. The signal from the optical square law detector 140 is pre-processed by a preamplifier and discriminator 150. This signal is then inputted into a signal processor 160 which can be an autocorrelator or a power spectrum analyzer and a computer 170 for processing as discussed previously. The autocorrelation function or power spectrum and any calculated parameters can be shown on a display 180.

Figure 2:
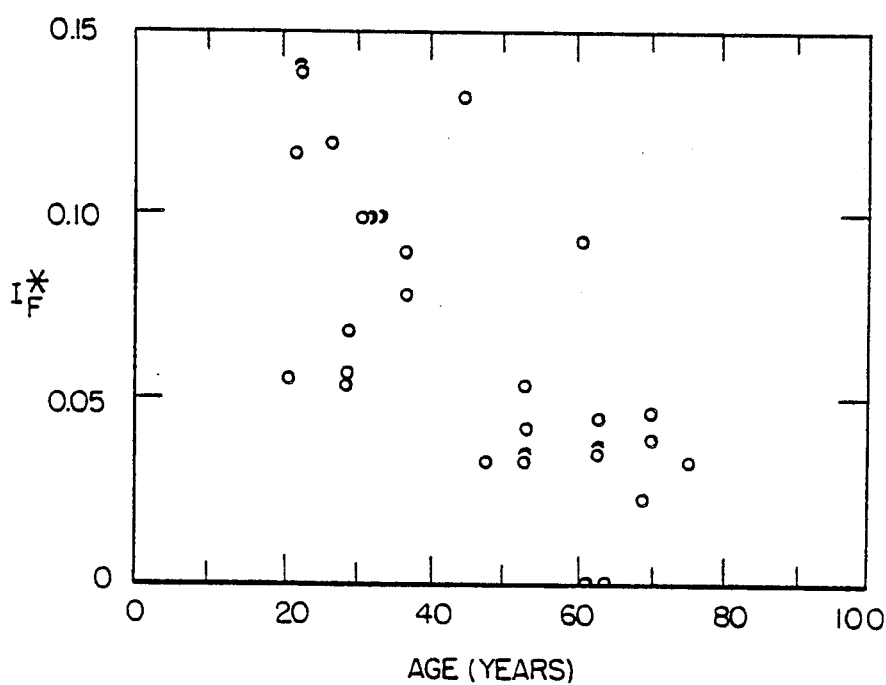
FIG. 2 is a plot of $I_f^*$ versus age at the position of the anterior nucleus in 29 subjects.

FIG. 2 is a presentation of measurements of $I_f^*$, the intensity of light scattered from the rapidly diffusing component, as a function of age as measured in the anterior nucleus in twenty-nine subjects. $I_f^*$ is obtained from the computer analysis of the correlation function and is directly proportional to $I_f$. The numerical constant relating $I_f^*$ to $I_f$ is determined entirely by instrumental gain factors. This graph shows clearly the statistically significant reduction in the concentration of this unaggregated protein as the lens nucleus ages.

The rate of diffusion $\Gamma_f$ this component was measured and found to be $1.5 \times 10^4 \text{ sec}^{-1} < \Gamma_f < 2.5 \times 10^4 \text{sec}^{-1}$. Using these values of $I_f$ and the value $K = 2.60 \times 10^5 \text{cm}^{-1}$, the diffusion coefficient $D_f$ is found to be $2.2 \times 10^{-7} \text{ cm}^2/\text{sec} < D_f < 3.7 \times 10^{-7} \text{cm}^2/\text{sec}$. These values can be compared with the value $2.23 \times 10^{-7} \text{cm}^2/\text{sec}$ found from light scattering studies on monodisperse alpha crystallins. It is possible, therefore, to associate the rapidly diffusing species with the unassociated α-crystallin proteins in the lens cell cytoplasm. The decrease of $I_f^*$ with age is consistent with biochemical studies showing the gradual disappearance of the alpha crystalline in the aging lens nucleus.

Figure 3:
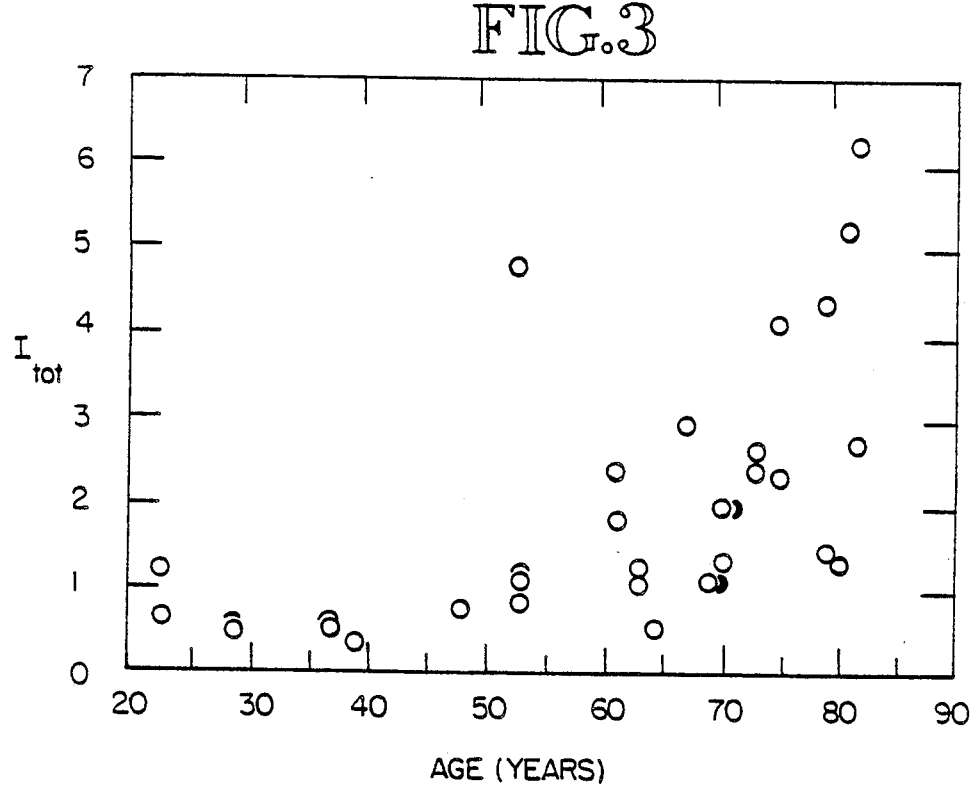
FIG. 3 is a plot of $I_{tot}$ versus age at the position of the central nucleus in 32 subjects.

In FIG. 3, $I_{tot}$ versus age for 33 persons as measured in the lens central nucleus is plotted. This graph shows that in the age group ranging from 20 to 50 years of age the scattered intensity remains relatively small. However, with aging beyond 60 years, a statistically significant increase of total scattered intensity with age is observed. This increase reflects age related development of senile nuclear cataract The results presented in FIG. 3 are consistent with previous transmission studies done by others This in-vivo data combined with the linear relationship between $I_{tot}$ and $I_s$ shown in FIG. 5 indicates that the development of senile cataract in the nucleus is associated with the conversion of the rapidly diffusing crystallin species to much larger slowly diffusing molecular aggregates.

Figure 4:
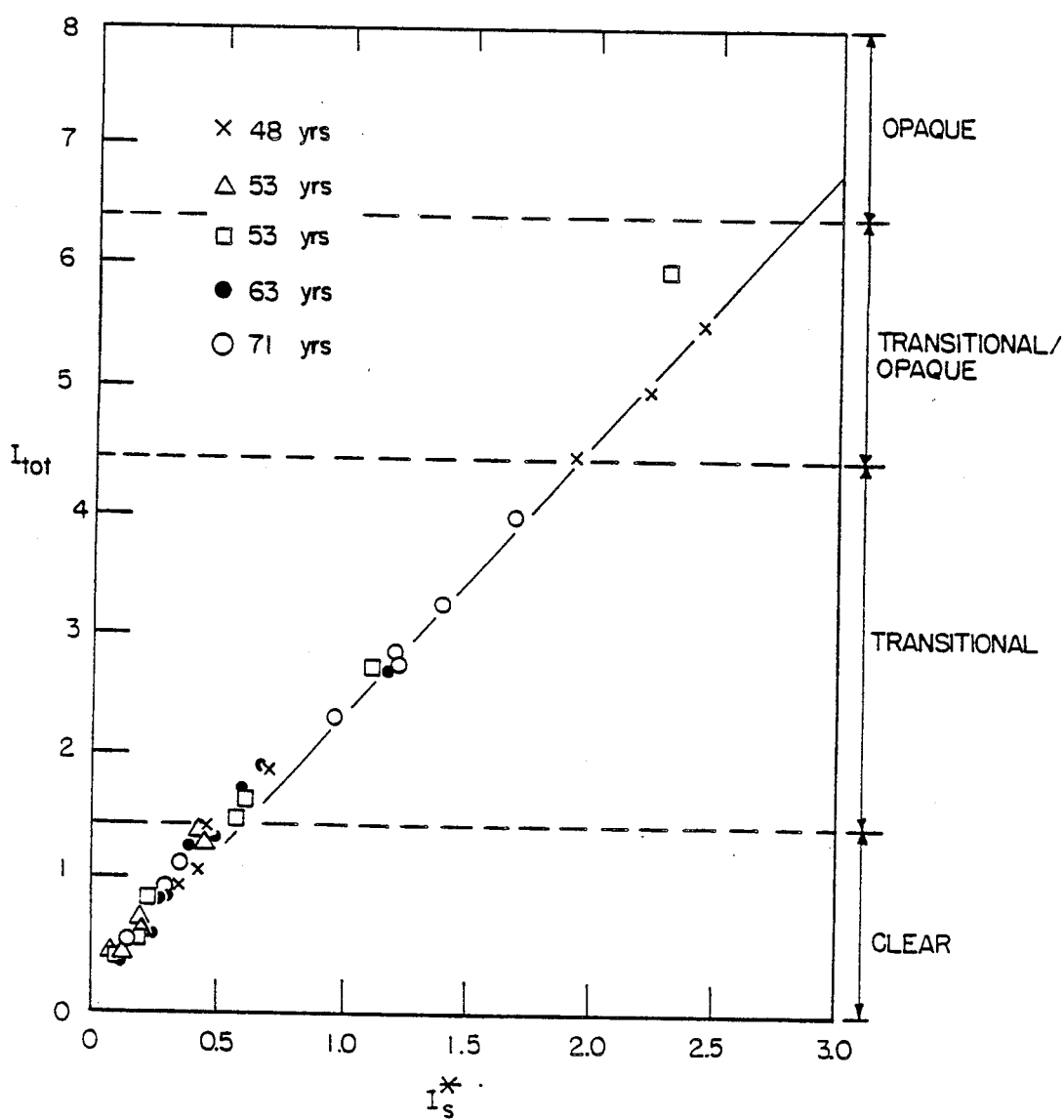
FIG. 4 is a plot of $I_{tot}$ versus $I_s^*$ for five preoperative cataract patients.

FIG. 4 represents the results of measurements made on five patients presenting preoperative lenticular opacification distributed at various locations in the lens. All the data were obtained at or near the optic axis of the lens. Typically five or six points ranging from anterior cortex to posterior nucleus were studied for each patient. The patients ranged in age from 48 to 71 years. $I_{tot}$ is plotted along the ordinate. Also, a qualitative visual designation of the degree of scattering associated with the observed values of $I_{tot}$ is indicated along this axis. On the abscissa, $I_s^*$ is plotted. $I_s^*$ is measured in the same units as $I_f^*$. As with $I_f^*$, the numerical constant relating to $I_s^*$ to $I_s$ is determined entirely by instrumental gain factors. The entire range over which $I_{tot}$ is measured corresponds to about a factor of 30 ranging from $I_{tot}$ of approximately 0.2 when $I_s^*$ is approximately 0 to $I_{tot}$ of approximately 6 when $I_s^*$ approximately 2.6. All measurements were confined to points which did not exhibit the multiple scattering associated with opaque regions. The range of $I_{tot}$ studied corresponds to the full domain of early cataract development. This domain corresponds to a factor of about 30 in total scattered intensity, as is consistent with the previous discussion. It is also observed that in this domain of scattering $I_{tot}$ is indeed linearly proportional to $I_s$ as predicted in Eqn. (9). This linear relationship holds both for all individuals studied, and for all the points studied in the lens of a single individual. Thus, the 48 year old patient (indicated by X on the Figure) has values for $I_{tot}$ ranging from $I_{tot}$ of approximately 0.9 to $I_{tot}$ of approximately 5.5. This is a quantitative expression of the fact that along the optic axis of this patient's lens, there are "normal" zones in which little conversion from fast to slowly diffusing proteins has occurred Here $0.9 \leq I_{tot} \leq 1.5$. Nevertheless, a few millimeters away, a considerable conversion to the slowly moving species has occurred Here the light scattering is much stronger: $4.0 \leq I_{tot} 5.5$. This graph clearly suggests that measurement of $I_{tot}$ and $I_s$ at a fixed position in the lens can permit a quantitative characterization of the degree of cataract development at that position. As cataractogenesis proceeds at a fixed position in the lens, $I_{tot}$ and $I_s$ along the "universal curve" of $I_{tot}$ versus $I_s$. On the other hand, the decrease of $I_{tot}$ and $I_s$ along the universal curve would correspond to an increase in fast diffusing species and a reduction the amount of slowly diffusing proteins. The finding that all the data from each person and each location falls on the $I_{tot}$ versus $I_s$ line clearly suggests that this "universal curve" can provide a very sensitive, linear and quantitative characterization of the degree of the molecular changes associated with early cataract. It should be kept in mind that visual or photographic detection of early cataract is characterized by a logarithmic response and is consequently less sensitive particularly in the early stages of cataractogenesis.

Figure 5:
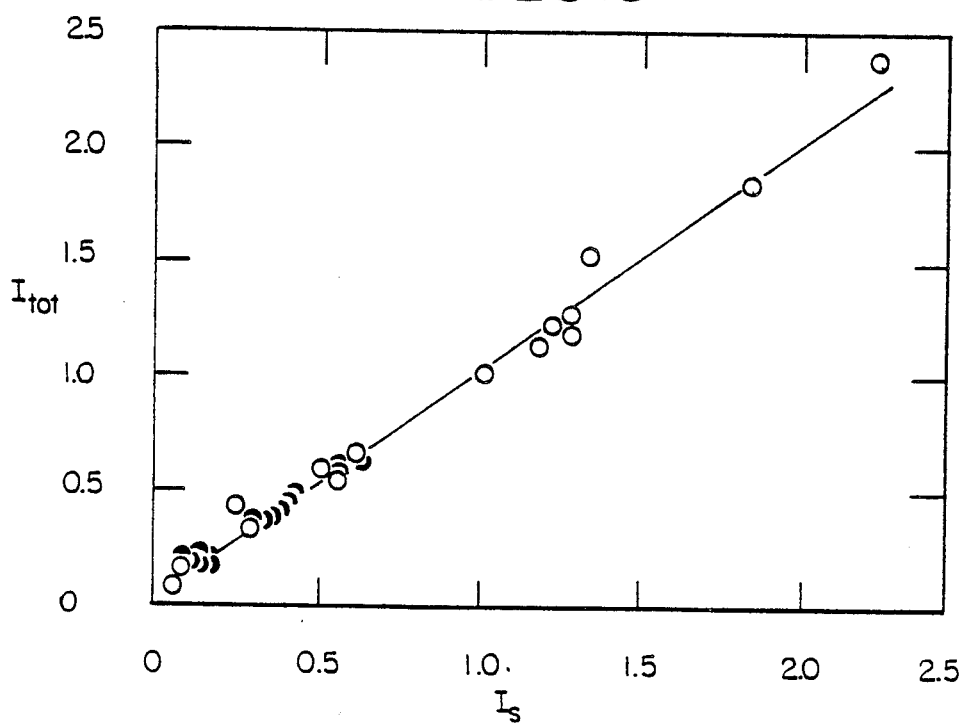
FIG. 5 is a plot of $I_{tot}$ versus $I_s$ at the position of the central nucleus in 28 subjects.

An investigation at fixed points in the lens of the slope $(1-S)$ of the linear relationship (Eqn. 9) between $I_{tot}$ and $I_s$ was also obtained. In FIG. 5 a plot of $I_{tot}$ versus $I_s$ as observed at the central nucleus for a subgroup of 28 patients with preoperative cataracts in the age group from 23-82 years is shown. This subgroup was selected to consist of individuals having no "opaque" or "transitional-opaque" regions in the lens nucleus. In analyzing the correlation function in these experiments the same units were chosen for the measurement of $I_{tot}$ and $I_s$. FIG. 5 shows unambiguously that in the central nucleus the relationship between $I_{tot}$ and $I_s$ is quite linear. From this graph it can be deduced that the magnitude of the slope parameter [see Eqn. 7 and 9] is given by $(1-S)=(0.96\pm0.02)$. $I_f^0 = 0.055\pm0.015$ at the center of the lens nucleus.

Similar studies were conducted on the same population at the anterior nucleus and the posterior nucleus. Table I below lists the measurements of $(1-S)$ and $I_f^0$ at each of these positions. The units for the determination of $I_s$ and $I_{tot}$ are the same and are determined by gain factors in the autocorrelation output channels. Thus the absolute magnitude of $I_f^0$ as listed in Table 1 is without physical significance. Nevertheless the magnitude of $I_f^0$ sets the scale against which cataract induced changes in $I_{tot}$ and $I_s$ are to be compared. The slope $(1-S)$ indicates that the important dimensionless factor S as defined in Eqn. 7 has the value $S=0.04\pm0.02$. This is consistent with the previous order of magnitude estimate of 0.1 for the value for S based on the assumption that the slowly diffusing corresponds to an element roughly 1000 Å in size.

TABLE 1

Measurements of the Slope and Intercept of the Relationship $I_{tot} = I_f^0 + (1-S)I_s$ at Various Positions in the Lens

| Position | Slope | $I_f^0$ |
|---|---|---|
| Anterior Nucleus | 0.96 ± 0.03 | 0.09 ± 0.02 |
| Central Nucleus | 0.96 ± 0.03 | 0.05 ± 0.02 |
| Posterior Nucleus | 0.95 ± 0.03 | 0.11 ± 0.03 |

EXAMPLE

The data shown in FIGS. 2-5 was obtained from a group consisting of a total of 49 individuals ranging in age from 21 to 82 years. Among these subjects nine had normal, clear lenses, and forty were pre-operative cataract patients with lenticular opacifications distributed at various locations. The results for this group are for measurements taken on the anterior cortex and three locations in the nucleus (anterior, central, posterior nucleus). All measurements were taken on or near the optical axis of the lens.

Light from a stable helium-neon laser($\lambda=632.8$ nm) was guided through the optics of a modified Reichert slip lamp microscope to the human lens. One milliwatt was focused to a 75 micron diameter cylindrical region in the lens. Posterior to the focal region in the lens, the beam diverged so that the irradiance on the retinal tissue was approximately 0.03 watts/cm$^2$ which was two orders of magnitude below the damage threshold for the retina which is 2 watts/cm$^2$ for 10 second exposures. The light scattered from the focused incident beam within the lens was visualized easily by the operator looking through the slit lamp microscope. This aperture could be located at the desired illuminated region of the tissue using the instrument's positioning controls. A small amount of light scattered into this aperature (about 3 coherence solid angles) was conducted to a photomultiplier tube through a fiber optic cable. A measurement was activated when a button was pressed which began the processing of the scattered light signal by the autocorrelator. The resulting autocorrelation function was analyzed by an IBM-XT personal computer which was programmed to fit each correlation function to the two-component exponential form shown in Eqn. 4. After fitting each curve, the computer presented the values for $I_{tot}$, $I_f$, $I_s$, $\Gamma_f$, $\Gamma_s$ and $\alpha$.

The values of of $\alpha$ determined by the computer for the measurements were within the range $0.18\pm0.02$. These values are close to an expected value of 0.166 which is determined from a calculation that takes into account the number of coherence solid angles, N, subtended by the pick-up aperature of the scattered light receiver: $\alpha$ (expected)$=\frac{1}{2}N$. For the aperature in the instrument N is approximately 3. From the close correspondence between the expected and measured values of $\alpha$, it can be concluded that the total scattered light is produced primarily by moving molecular components and that scattering from large, static structures is relatively small.

The autocorrelator used was a Coulter/Langely-Ford digital autocorrelator and contained 128 data channels. For each location in a subject's lens, measurements were taken at two sample times: 5 microseconds and 50 microseconds. The data were accumulated for 3 seconds for each measurement. The autocorrelation function obtained with the 5 microsecond sample time, when analyzed, provided the parameters $I_f$, $\Gamma_f$ and $I(tot)$. The autocorrelation function obtained with the 50 microsecond sample time provided $I_s$, $\Gamma_s$ and $I(tot)$. The apparent scattering angle (i.e. outside the eye) was 135°. Refraction at the air-cornea interface made the actual internal scattering angle slightly larger. Based on calculations, which take into account the index of refraction of the ocular tissues, the radius of curvature of the cornea, and the measurement location within the lens, it is possible to estimate that the actual scattering angle (i.e. inside the eye) was 138.5°. Using $\theta=138.5°$, the value of the wave vector K for the scattering process was calculated to be $K=2.60\times10^5$ cm$^{-1}$. In this calculation the value 1.40 was used for the index of refraction of the human lens.

Equivalents

Those skilled in the art will recognize, or be able to ascertain, using no more than routine experimentation, many equivalents to the specific embodiment of the invention described herein. For example, the delivery, observation, control and collection optics are not intended to be solely limited to the embodiments described herein, but rather are intended to extend to any optical system suitable for these purposes Such equivalents are intended to be encompassed by the following claims.

We claim:

1. A method for in-vivo inspection of ocular tissue at a specific site comprising:
   (a) providing a source of substantially monochromatic, coherent, collimated light;
   (b) focusing light from the source on a first measurement location of a subject's ocular tissue wherein said first measurement location corresponds to the clearest area of the subject's ocular tissue;
   (c) collecting light scattered by the first measurement location;
   (d) converting the light scattered by the first measurement location into an electrical signal representative of the intensity of the light scattered by the first measurement location ($I_1^\rho$);
   (e) storing the value of $I_1^\rho$ for later reference;
   (f) focusing light from the source on a second measurement location of a subject's ocular tissue wherein said second measurement location corresponds to the area of the subject's ocular tissue which is to be examined;
   (g) collecting the light scattered by the second measurement location;
   (h) converting the light scattered by the second measurement location into an electrical signal representative of the intensity of the light scattered by the second measurement location ($I_{tot}$); and,
   (i) comparing the value of $I_{tot}$ to that of $I_1^\rho$ to determine the degree of cataractogenesis at the second measurement location of the ocular tissue.

2. A method for in-vivo inspection of ocular tissue at a specific site comprising:
   (a) providing a source of substantially monochromatic, coherent, collimated light;
   (b) focusing light from the source on a calibrating element;
   (c) collecting light scattered by the calibrating element;
   (d) converting light scattered by the calibrating element into an electrical signal representative of the intensity of the light scattered by the calibrating element ($I_1^\rho$);
   (e) storing the value of $I_1^\rho$ for later reference;
   (f) focusing light from the source on a measurement location of a subjects ocular tissue wherein said measurement location corresponds to the area of the subject's ocular tissue which is to be examined;
   (g) collecting the light scattered by the measurement location;
   (h) converting the light scattered by the measurement location into an electrical signal representative of the intensity of the light scattered by the measurement location ($I_{tot}$); and,
   (i) comparing the value of $I_{tot}$ to that of $I_1^\rho$ to determine the degree of cataractogenesis at the measurement location of the ocular tissue.

3. A method as in claim 2 wherein the calibrating element scatters light of an intensity $I_1^\rho$ corresponding to a previously determined average $I_1^\rho$ value of light scattered from normal clear regions of a normal lens.

4. A method as in claim 2 wherein the calibrating element comprises a suspension of polystyrene latex spheres in water.

* * * * *